(12) United States Patent
Marion

(10) Patent No.: US 8,241,675 B2
(45) Date of Patent: Aug. 14, 2012

(54) ELEMENTAL INDIUM AND INDIUM COMPOUNDS SUITABLE FOR HUMAN, MAMMAL, FOWL AND REPTILIAN NUTRITION

(76) Inventor: Joseph B. Marion, Santa Barbara, CA (US)

( * ) Notice: Subject to any disclaimer, the term of this patent is extended or adjusted under 35 U.S.C. 154(b) by 972 days.

(21) Appl. No.: 12/231,876

(22) Filed: Sep. 8, 2008

(65) Prior Publication Data

US 2010/0062080 A1 Mar. 11, 2010

(51) Int. Cl.
*A61K 33/24* (2006.01)
*A61P 3/02* (2006.01)

(52) U.S. Cl. ........................................ 424/650

(58) Field of Classification Search .................. None
See application file for complete search history.

(56) References Cited

U.S. PATENT DOCUMENTS 4,182,754 A * 1/1980 Bonadio ................. 424/650
6,007,847 A * 12/1999 Bonadio ................. 424/650
2007/0196467 A1 * 8/2007 Hack et al. ............. 424/464

* cited by examiner

*Primary Examiner* — James H. Alstrum-Acevedo
*Assistant Examiner* — Daniel L Branson
(74) *Attorney, Agent, or Firm* — Baxam Law Group, LLC; Deanna L. Baxam

(57) ABSTRACT

Use of safe forms of elemental indium and associated compounds at approximately ¼ to 1 mg per 50 pounds of body weight in water-soluble liquid solution taken away from other foods orally into the mouth and stomach to enhance human, mammal, fowl and reptile nutrition and metabolism.

9 Claims, No Drawings

ELEMENTAL INDIUM AND INDIUM COMPOUNDS SUITABLE FOR HUMAN, MAMMAL, FOWL AND REPTILIAN NUTRITION

(4b) CROSS REFERENCE TO RELATED APPLICATIONS

| | | | |
|---|---|---|---|
| 3,937,806 | February 1976 | Cooley | 424/52 |
| 4,182,754 | January 1980 | Bonadio | 424/650 |
| 4,359,477 | November 1982 | Rogers | 424/287 |
| 4,454,162 | June 1984 | Schanze | 426/74 |
| 4,591,506 | May 1986 | Bonadio | 424/131 |
| 5,739,106 | April 1998 | Rink et al. | 514/12 |
| 5,763,480 | June 1998 | Schlesinger | 514/476 |
| 6,007,847 | December 1999 | Bonadio | 424/650 |

STATEMENT OF FEDERALLY SPONSORED RESEARCH

None.

FIELD OF THE INVENTION

This invention is about using the trace mineral element #49 indium and all its humanly-usable compounds in addition to indium-sulfate that are beneficial for human, mammal, fowl and reptile nutrition daily for life, to enhance the good health, glandular functions, performance, motion, clarity of thought, immunity, and longevity of people, pets, livestock, all mammals, fowl and reptiles.

BACKGROUND OF THE INVENTION

The present invention is about using the trace mineral element indium, number 49 on the Periodic Table of Elements, in water-soluble forms as a nutritional supplement in humans, mammals, fowl and reptiles. The indium element appears in nature in trace amounts, being the seventh rarest element, and is hard to absorb being generally insoluble in water. This problem of inabsorption has been solved by Bonadio's U.S. Pat. No. 6,007,847 entitled "Methods for Administering Nutritional Indium," which specifies taking indium-sulfate all by itself, away from all foods, approximately 7 to 10 hours after eating or first thing in the morning, by liquid drops taken orally on the back of the tongue to be swallowed into the stomach, then waiting ten to thirty minutes before consuming other drink or food, for maximum absorption. It is believed that some indium may be absorbed under the tongue also, but perhaps not so efficiently. This patent relates to using every other form of pure elemental indium and its compounds for nutritional purposes.

The first scientists to do any nutritional studies of indium were Dr. Henry A. Schroeder and assistants Balssa, Mitchner, Kanisawa, Nason and Vinton of Dartmouth University Medical School in 1964 to 1973 who published thirteen studies of indium effects on mice, the main papers propounded in the Journal of Nutrition Vol. 101-10, pages 1431-1438 (1971) entitled "Scandium . . . Indium in Mice, Effects On Growth & Lifespan;" in the Journal of Nutrition Vol. 104, pages 157-168 (1974); and in the Journal of Nutrition Vol. 106-2, pages 198-203 (1976) entitled "Interactions of Trace Metals In Mouse Tissues." These studies proved indium to be non-toxic in thousands of mice experiments, and therefore safe for all mammals including humans if taken by certain methods within appropriate dosage limits.

W. E. Cooley found indium prevents tooth decay in U.S. Pat. No. 3,937,806. H. J. Rogers found indium useful for enterochelin complexes on *klebsiella pneumonia* in U.S. Pat. No. 4,359,477. Schlesinger found indium inhibits cell-mediated disorders in U.S. Pat. No. 5,763,480. Bonadio's experimental research on indium was corroborated by Joseph B. Marion's findings and user reports published in the book "Indium, New Mineral Discovery of The 21st Century by Information Pioneers Publisher 2003. Dr. Robert Lyons published similar nutritional findings of indium in the books "Indium, the Missing Link Mineral" by New Health Press 2001; and "The Anti-Aging Health-Promoting Mineral Indium" by Banner Health Books 2004, also finding increased athletic strength, power, speed and recuperative tendencies. In a nutshell, indium may be the greatest nutritional discovery of the 21st century because it allows level-2 glandular performance previously unknown or thought impossible.

BRIEF SUMMARY OF THE INVENTION

The present invention expands the patentable indium compounds to be used in human, mammal, fowl and reptilian nutrition beyond Bonadio's patented indium sulfate use in humans, to encompass elemental indium in any water-soluble form found to be safe for human consumption, including angstrom indium, atomized indium, energetic indium, lasared indium, molecular indium, monatomic indium, any indium chelates, indium-ascorbate, indium-aspartate, indium-orotate, any indium compounds, indium-antimony, indium-arsenide, indium-carbonate, indium-chloride, indium-gallide, indium-oxide, indium phosphide, indium-selenide, indium-telluride, indium-trichloride, et al. when taken in tiny amount orally by itself away from all foods so as to prevent its binding inabsorption with other organic elements and compounds.

RECOMMENDED USE OF THE INVENTION

The nutritional use of pure elemental indium and any safe indium compound daily for life in a water solution is to be taken orally by itself away from all foods for maximum effect, ideally 7-10 hours after eating or drinking anything but pure water, although some efficasy may be experienced taken at other times. The indium element or compound can be swished in the mouth or under the tongue, but is mainly to be swallowed into the stomach, then wait ten minutes before eating or drinking anything if normally active, or 20 minutes if inactive, or 30 minutes if bed-bound. Unless fasting, this is best accomplished the first thing in the morning upon awakening. The recommended amount of indium element ranges approximately from ¼ mg. upwards to 10 mg. to be taken once daily in one morning dose depending on physical constitution, lightweight persons such as children or females taking the smallest dosage, and heavier weight persons or mammals taking larger doses, approximately from ¼ milligram (mg.) to 1 mg. per 50 pounds of body weight. Start with a low dose, and gradually raise to normal usage after 1-4 weeks inversely proportionate to how (hyper)allergic or toxic one may be, corresponding to how one reacts to the small amount first taken. Taking too much indium too soon may cause the liver and immune organs to offload excess toxins too fast, making one feel headache, upset stomach, nausea, etc. at first. If an adult, take one mg./drop pure indium per day the first week, two mg./drops pure indium per day the second week, and work up to one's normal amount of 3-4 mg./drops pure indium daily by the third or fourth week for 150-200 lbs.

of body weight to prevent feeling a precipitous cleansing reaction, and to allow disparate glands to remineralize equally. Some especially healthy and robust persons report results quicker when taking 1-2 times the recommended amount, but that is strictly a decision choice of their own after consultation with their physician.

It is helpful to science if users write down their age, weight, sex, and any health problems or feelings they have prior to taking nutritional indium, then chart the progress as one takes nutritional indium to document its health-changing benefits thereafter experienced. The same is true using indium for pets, livestock, fowl, and reptiles at home, on farms, in zoos and even wild habitats in drinking water put out for such purpose.

THEORY OF OPERATION

The taking of nutritional indium improves other minerals' absorption into human, mammal, fowl and reptile tissues from about 60 to 300 percent (60-300%), depending on which mineral and what tissue is examined. Indium appears to enable cell genetic DeoxyRiboNucleic Acids (DNA) to pick up a fuller complement of mineral fuels, thus fulfilling the intrinsic DNA potential to operate at a higher expression of its genetic powers. This improved mineral uptake allows glands to rebuild to a higher level of function, to level-two of performance that was previously unattainable, normalizing or heightening glandular secretions of hormones and neurotransmitters that direct metabolism to a youthful, optimal level, staving off the effects of ailments and aging longer. This is especially important for the master glands of the pituitary-hypothalamus feedback loop which controls the other endocrine glands. This effect tends to dispel or put into remission chronic mineral-deficiency imbalances or diseases that may be a challenge to one's potential wellness lifestyle, and allows a happier mood, less pain, and the "feeling of easy living."

BENEFITS OF THE INVENTION

This indium nutritional invention usage allows expansion of the present estimated 4-14 percent (4-14%) operational limitation of mental powers and glandular resources in humans, mammals, fowl, and reptiles up to 60-300% heightened expression, providing greater peace of mind, mental clarity, immune functions, better safety and health for users. It allows the gradual reduction in aching, nagging, chronic diseases or impediments formerly thought inevitable or incurable, such as low thyroid, insomnia, diabetes, glaucoma, anxiety, depression, attention deficit disorder, pain, arthritis, circulatory impediments, menopause hot flashes, makes for healthy skin and hair, restores gray hair to normal color, improves immune functions against colds, allergies, cancer and tumors, allows for better sexuality, libido, prostate health, growth, athletic prowess, and may lessen or prevent birth defects due to heightened mineralization and metabolism. Indium supports a timely, less painful, less traumatic childbirthing process due to heightened Chromium to Insulin to Relaxin metabolisms. All the benefits of indium supplementation may go beyond those presently catalogued, providing a new paradigm standard of mental consciousness, expression of will power, and performance of human and animal functions, a new and enhanced technological and cultural achievement economizing fewer health care costs, health insurance payouts, ailment downtime, pain and suffering for humans, pets, and livestock.

DETAILED DESCRIPTION OF THE INVENTION

This invention is made possible by using any of the available forms of water-soluble elemental indium and indium compounds that prove to be safe and efficacious for human, mammal, fowl, and reptile nutrition, including any water-soluble form of angstrom indium, atomized indium, energetic indium, lasared indium, molecular indium, monatomic indium, any indium chelates, indium-ascorbate, indium-aspartate, indium-orotate, any indium compounds, indium-antimony, indium-arsenide, indium-carbonate, indium-chloride, indium-gallide, indium-oxide, indium phosphide, indium-selenide, indium-telluride, indium-trichloride, et al. Such indium forms may enhance health powers and disease resistance beyond the present mineral deficiencies' limitations to level-2 of glandular functions and associated improved consciousness.

The indium element or compound is mixed with distilled water, purified water, energized or catalyst-altered "wetter" water in such a ratio so that the mg. per drop (mg./drop) pure indium dosage is between 1/4 to 1 mg. pure indium per drop for each fifty (50) pounds of human or mammal body weight; or 1/10 of that amount of pure indium for each 5 pounds of a small mammal, fowl, or pet's weight; to ten times that amount of pure indium for each 500 pounds of livestock, horse, cattle or zoo animal body weights. For experimental purposes, this recommended amount may be doubled or tripled in healthy individuals or animals for a limited time to determine any extra benefit results.

The appropriate mixture is taken or given on an empty stomach first thing in the morning before food or drink, with a delay of ten minutes or more before other food or drink is consumed. The admixture can also be provided in pet, livestock, fowl or other animals' water pans or troughs for self-service of the nutrient. Spray or atomizers of the admixture may be used, but are less efficient with back-blow wasting some of the nutrient.

The invention claimed is:

1. A method of supplementing human and animal nutrition comprising administering, by oral ingestion, a dosage amount of an aqueous solution which comprises from 0.025 to 10.0 mg per drop of an elemental indium or indium compound selected from the group consisting of angstrom indium, energetic indium, lasared indium, molecular indium, indium ascorbate, indium aspartate, indium orotate, indium-arsenide, indium gallide, indium phosphide, indium telluride, indium trichloride and combinations thereof, and immediately swallowing substantially all of the dosage amount after ingestion.

2. The method of claim 1, wherein the aqueous solution is formed from the dissolution of the indium compound in water selected from distilled water, purified water, energized water, or wetter water.

3. The method of claim 1, wherein the aqueous solution provides a dosage amount of from 0.025 to 0.1 mg per drop.

4. The method of claim 1, wherein the aqueous solution provides a dosage amount of from 0.25 to 1.0 mg per drop.

5. The method of claim 1, wherein the aqueous solution provides a dosage amount of from 2.5 to 10.0 mg per drop.

6. The method of claim 1, further comprising adding a dosage of the aqueous solution to drinking water before oral ingestion.

7. A method of supplementing human nutrition comprising administering, by oral ingestion, a dosage amount of an aqueous solution which comprises from 0.25 to 1.0 mg per drop of an elemental indium or indium compound selected from the group consisting of angstrom indium, energetic indium, lasared indium, molecular indium, indium ascorbate, indium aspartate, indium orotate, indium-arsenide, indium gallide, indium phosphide, indium telluride, indium trichloride and combinations thereof per 50 pounds of body weight, immediately swallowing substantially all of the dosage amount; and waiting 10 minutes or more before eating or drinking.

8. The method of claim 7, wherein the aqueous solution is formed from the dissolution of the indium compound in water selected from distilled water, purified water, energized water, or wetter water.

9. The method of claim 7, further comprising adding a dosage of the aqueous solution to drinking water before oral ingestion.

* * * * *